US009840714B2

(12) United States Patent
Hiei et al.

(10) Patent No.: US 9,840,714 B2
(45) Date of Patent: *Dec. 12, 2017

(54) METHOD FOR PROMOTING EFFICIENCY OF GENE INTRODUCTION INTO PLANT CELLS

(75) Inventors: Yukoh Hiei, Shizuoka (JP); Keisuke Kasaoka, Oyama (JP); Yuji Ishida, Shizuoka (JP)

(73) Assignee: JAPAN TOBACCO INC., Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 13/099,917

(22) Filed: May 3, 2011

(65) Prior Publication Data

US 2011/0209251 A1  Aug. 25, 2011

Related U.S. Application Data

(60) Division of application No. 12/902,631, filed on Oct. 12, 2010, now Pat. No. 7,960,611, which is a continuation of application No. 10/089,696, filed as application No. PCT/JP00/05213 on Aug. 3, 2000, now abandoned.

(51) Int. Cl.
C12N 15/82 (2006.01)

(52) U.S. Cl.
CPC ..... *C12N 15/8205* (2013.01); *C12N 15/8201* (2013.01); *C12N 15/8207* (2013.01)

(58) Field of Classification Search
CPC ............ C12N 15/8205; C12N 15/8201; C12N 15/8207; A01H 5/00
USPC .......................... 800/294, 278; 435/468, 469
See application file for complete search history.

(56) References Cited

U.S. PATENT DOCUMENTS

| | | | |
|---|---|---|---|
| 4,693,976 A | | 9/1987 | Schilperoort et al. |
| 4,940,838 A | | 7/1990 | Schilperoort et al. |
| 5,272,072 A | * | 12/1993 | Kaneko .............. C12N 15/8206 435/460 |
| 5,589,626 A | * | 12/1996 | Hain et al. .................... 800/279 |
| 5,591,616 A | | 1/1997 | Hiei et al. |
| 5,731,179 A | | 3/1998 | Komari et al. |
| 5,981,840 A | * | 11/1999 | Zhao .................. C12N 15/8205 435/320.1 |
| 6,215,051 B1 | | 4/2001 | Yu et al. |
| 6,316,694 B1 | * | 11/2001 | Dormann ........... C12N 15/8205 435/410 |
| 6,329,571 B1 | | 12/2001 | Hiei |
| 6,362,393 B1 | | 3/2002 | Konzak et al. |

FOREIGN PATENT DOCUMENTS

| | | |
|---|---|---|
| EP | 0 116 718 B1 | 8/1984 |
| EP | 0 159 418 B1 | 10/1985 |
| EP | 0 504 869 A2 | 9/1992 |
| EP | 0 672 752 A1 | 9/1995 |
| EP | 0 927 765 A1 | 7/1999 |
| EP | 1 136 560 A1 | 9/2001 |
| JP | 2000-342255 A | 12/2000 |
| JP | 2001-029075 A | 2/2001 |
| WO | WO 96/29419 A1 | 9/1996 |

OTHER PUBLICATIONS

Bouck. Stratification and subsequent behavior of plant cell organelles. The Journal of Cell Biology, vol. 18 (1963) pp. 441-457.*
Cheng et al. Invited review: Factors influencing Agrobacterium-mediated transformation of *monocotyledonous* species. In Vitro Cell. Dev. Biol.-Plant 40:31-45 (2004).*
Cheng et al. Rice transformation by Agrobacterium infection. Methods in Biotechnology, vol. 3: Recombinant Proteins from Plants: Production and Isolation of Clinically Useful Compounds, 1997, pp. 1-9.*
Cheng et al. Rice Transformation by Agrobacterium Infection. Methods in Biotechnology, vol. 3: Recombinant Proteins form Plants: Production and Isolation of Clinically Useful Compounds, Humana Press Inc., Totowa, NJ, pp. 1-9, 1997.*
Choi et al. High Frequency of Plant Production via Somatic Embryogenesis for Callus or Cell Suspension Cultures in Eleutherococcus senticosus. Annals of Botany 83: 309-314, 1999.*
Masuda et al. Callus formation and plant regeneration from rice protoplasts purified by density gradient centrifugation. Plant Science, 62 (1989) 237-246.*
Hiei et al. Transformation of rice mediated by Agrobacterium tumefaciens. Plant Molecular Biology 35: 205-218, 1997.*
Choi et al. High Frequency of Plant Production via Somatic Embruogenesis form Callus or Cell Suspension Culture in Eleutherococcus senticosus, Annals of Botany 83: 309-314, 1999.*
Hiei et al. Transformation of rice mediated by Agrobacterium tumefaciens, Plant Molecular Biology 35: 205-218, 1997.*
A. Hoekema et al., Nature, vol. 303, (May 1983), pp. 179-180.
Bruce Watson et al., Journal of Bacteriology, vol. 123, No. 1, (Jul. 1975), pp. 255-264.
Christina L. Hartman et al., Bio/Technology, vol. 12, (Sep. 1994), pp. 919-923.
Chu Chin-Ching, Excerpt from the Sino-Australian Plant Tissue Culture Symposium, held May 25-30, (Aug. 1978), pp. 43-50.
Dennis Bidney et al., Plant Molecular Biology, vol. 18, (1992), pp. 301-313.
Dodds et al., Experiments in Plant Tissue Culture, 2nd ed., 1988, Cambridge University Press, pp. 139-141.
Elizabeth E. Hood et al., Biotechnology, vol. 2, (1984), pp. 702-709.
Elizabeth E. Hood et al., Journal of Bacteriology, vol. 168, No. 3, (Dec. 1986), pp. 1291-1301.

(Continued)

*Primary Examiner* — June Hwu
(74) *Attorney, Agent, or Firm* — Birch, Stewart, Kolasch & Birch, LLP

(57) ABSTRACT

A method for gene introduction by which higher efficiency for gene introduction than that by the conventional *Agrobacterium* method may be attained simply and without injuring the tissue is disclosed. According to the method of the present invention, the efficiency of gene introduction into plant cells by a bacterium belonging to genus *Agrobacterium* is promoted by accompanying centrifugation of the plant cells or plant tissue.

10 Claims, 4 Drawing Sheets

(56) References Cited

OTHER PUBLICATIONS

Elizabeth E. Hood et al., Plant Physiol., vol. 83, (1987), pp. 529-534.
Elizabeth E. Hood et al., Transgenic Research, vol. 2, (1993), pp. 208-218.
Forreiter et al., "Stable ransformation of an arabidopsis cell suspension culture with firefly luciferase providing a cellular system for analysis of chaperone actity in vivo", the Plant Cell, vol. 9 (1997) pp. 2171-2181.
Gary Ditta et al, Proc. Natl. Acad. Sci. USA, vol. 77, No. 12, (Dec. 1980), pp. 7347-7351.
Harold N. Trick et al., Transgenic Research, vol. 6, (1997), pp. 329-336.
Heng Zhong et al., Plant Cell Reports, vol. 13, (1993), pp. 1-6.
Hong-Quing Li et al., Nature Biotechnology, vol. 14, (Jun. 1996), pp. 736-740.
I. Potrykus et al., Theor. Appl. Genet, vol. 54, (1979), pp. 209-214.
Jesus Escudero et al., Molecular Biology Protocols, The Maize Handbook (1994), pp. 598-603.
Keith Lindsey et al., Plant Tissue Culture Manual, vol. B7, (1991), pp. 1-13.
Kinya Toriyama et al., Plant Science, vol. 41, (1985), pp. 179-183.
L. Xiao et al., Plant Cell Reports, vol. 16, (1997), pp. 874-878.
Lyznik et al. "Heat-inducible expression of FLP gene in maized cells", The Plant Journal vol. 8, No. 2 (1995) pp. 177-186.
Mary-Dell Chilton et al, Proc. Nat. Acad. Sci. USA, vol. 71, No. 9, (Sep. 1974), pp. 3672-3676.
Michael Bevan, Nucleic Acids Research, vol. 12, No. 22, (1984), pp. 8711-8721.
P. Zambryski et al., EHBO, vol. 2, (1983), pp. 2143-2150.
Plant Molecular Biology Manual, Kluwer Academic Publishers, (1988), pp. PMAN A3/2-A3/19.
R.B. Horsch et al., Science, vol. 227, (Mar. 8, 1985), pp. 1228-1231.
Rhodora R. Aldemita et al., Planta, vol. 199, (1996), pp. 612-617.
Richard A. Jefferson, Plant Molecular Biology Reporter, vol. 5, No. 4, (1987), pp. 387-405.
Richard G.F. Visser, Plant Tissue Culture Manual, vol. B5, (1991), pp. 1-9.
Robert T. Fraley et al., Bio/Technology, vol. 3, (Jul. 1985), pp. 629-635.
Robert T. Fraley et al., Proc. Natl. Acad. Sci. USA, vol. 80, (Aug. 1983), pp. 4803-4807.
Sheila McCormick, Plant Tissue Culture Manual, vol. B6, (1991), pp. 1-9.
Shouguang Jin et al., Journal of Bacteriology, vol. 169, No. 10, (Oct. 1987), pp. 4417-4425.
Shozo Ohta et al., Plant Cell Physiol., vol. 31, No. 6, (1990), pp. 805-813.
Stephen G. Rogers et al., Methods for Plant Molecular Biology, (1988), pp. 423-437.
T. Komari et al., Current Opinion in Plant Biology, vol. 1 (1998) pp. 161-165.
T. Komari, Theor. Appl. Genet, vol. 80, (1990), pp. 167-171.
Technical Resource Convert between times gravity (xg) and centrifuge rotor speed (RPM). Pierec Biotechnology, Inc. Jan. 2005 [online], retrieved on Jan. 4, 2007, from the Internet <http://www.piercenet.com/files/TR0040dh4-Centrifuge-speed.pdf> one page.
Toshihiko Komari et al., Journal of Bacteriology, vol. 166, No. 1 (Apr. 1996) pp. 88-94.
Toshihiko Komari et al., Molecular Improvement of Cereal Crops, (Copyright 1999), pp. 43-82.
Toshihiko Komari et al., The Plant Journal, vol. 10, No. 1, (1996), pp. 165-174.
Toshihiko Komari, Plant Cell Reports, vol. 9, (1990), pp. 303-306.
Toshihiko Komari, Plant Science, vol. 60, (1989), pp. 223-229.
Toshio Murashige et al., Physiologia Plantarum, vol. 15, (1962), pp. 473-497.
Y. Asano et al., Plant Cell Reports, vol. 17, (1998), pp. 963-967.
Y. Saito et al., Theor. Appl. Genet, vol. 83, (1992), pp. 678-683.
Yoshito Asano et al., Plant Cell Reports, vol. 13, (1994), pp. 243-246.
Yuji Ishida et al., Nature Biotechnology, vol. 14, (Jun. 1996), pp. 744-751.
Yukoh Hiei et al., The Plant Journal, vol. 6, No. 2, (1994), pp. 271-282.
Bouck, G.B., "Stratification and Subsequent Behavior of Plant Cell Organelles," J Cell Biol, Aug. 1963, vol. 18, pp. 441-457.
International Search Report for PCT/JP00/05213 dated Oct. 31, 2000, p. 1.
K. Lindsey, Plant Tissue Culture Manual, Supplement 1, (1992), pp. 1-2.
Keith Lindsey et al., "Regeneration and transformation of sugarbeet by Agrobacterium tumefaciens", Plant Tissue Culture Manual, vol. B7, Kluwer Academic Publishers, edited by K. Lindsey, (1991), pp. 1-13.
Methods for Plant Molecular Biology, Academic Press, Inc., edited by Arthur Weissbach, (1988), pp. 1-2.
Richard G.F. Visser, "Regeneration and transformation of potato by Agrobacterium tumefaciens", Plant Tissue Culture Manual, vol. B5, Kluwer Academic Publishers, edited by K. Lindsey, (1991), pp. 1-9.
Sheila McCormick, "Transformation of tomato with Agrobacterium tumefaciens", Plant Tissue Culture Manual, vol. B6, Kluwer Academic Publishers, edited by K. Lindsey, (1991), pp. 1-9.
Stephen G. Rogers et al. "Gene Transfer in Plants: Production of Transformed Plants Using Ti Plasmid Vectors", Methods for Plant Molecular Biology, Academic Press, Inc., edited by Arthur Weissbach, (1988), pp. 423-436.

* cited by examiner

METHOD FOR PROMOTING EFFICIENCY OF GENE INTRODUCTION INTO PLANT CELLS

This application is a Divisional of U.S. application Ser. No. 12/902,631 filed on Oct. 12, 2010, now U.S. Pat. No. 7,960,611 issued Jun. 14, 2011, which is a Continuation of U.S. application Ser. No. 10/089,696 filed on Jul. 24, 2002, now abandoned, which is a national phase of PCT Application No. PCT/JP00/05213 filed on Aug. 3, 2000, and for which priority of all the aforementioned applications is claimed under 35 U.S.C. §120; the entire contents of all are hereby incorporated by reference.

TECHNICAL FIELD

The present invention relates to a method for promoting efficiency of gene introduction into plant cells.

BACKGROUND ART

The method for transformation using *Agrobacterium* has a number of excellent features including, in general, the high efficiency, the small number of copies of the introduced gene, the feature that the gene may be introduced without fragmenting a specific region called T-DNA, and the feature that the frequency of mutation occurred during cultivation is low because transformants may be obtained by cultivation for a short period of time. Therefore, the method is widely used as the most useful method for transforming various plants.

Although the *Agrobacterium* method is an extremely excellent method for transforming plants, whether the transformation is successful or not and the transformation efficiency largely varies depending on the plant species, genotype and the plant tissue used (Potrykus et al. 1998 (Reference (33))). That is, there are species with which the transformation has not been successful, and species with which the transformation may be attained only with limited varieties. Further, there are species with which the tissue to be used is limited so that a large amount of materials cannot be treated. To prepare a practical variety by genetic recombination, it is necessary to prepare a large number of transformed plants and to select the line having the desired character therefrom. However, at present, the type of plants with which a large number of transformed plants may be prepared for this purpose is limited. Thus, to develop an improved method by which this problem may be overcome is strongly demanded.

Although the method for transformation via *Agrobacterium* differs in the starting material, composition of the culture medium and the like, it is almost common to the *Agrobacterium* method that the method comprises making a tissue which is a starting material contact a suspension of *Agrobacterium*, selecting transformed cells after co-culturing, and growing transformed plants. The *Agrobacterium* is infected without performing a special treatment except for sterilization treatment which is carried out as required (Rogers et al. 1988 (Reference (34)), Visser 1991 (Reference (38)), McCormick 1991 (Reference (29)), Lindsey et al. 1991 (Reference (28))). Thus, studies for improving transformation system has been carried out mainly on the *Agrobacterium* strain, constitution of the vector, composition of medium, types of selection marker gene and promoter, the type of the tissue used as the material, and the like.

On the other hand, studies for changing the plant tissue before infection of *Agrobacterium* to a physiological state in which the genes are likely to be introduced have been scarcely made. If the physiological state of the tissue can be changed to such a physiological state by a simple treatment, the method is very useful, and it is expected that, in addition to the promotion of the transformation efficiency, transformation may be attained for the species or genotypes with which transformation has been hitherto difficult, that is a prominent effect. Known studies about pretreatment of plant tissue include particle gun treatment (Bidney et al., 1992 (Reference (5))) and ultrasonication treatment (Trick et al., 1997 (Reference (37))). Both of these methods aim at promoting invasion of bacteria into the plant tissue by physically injuring the tissue, so as to increase the number of plant cells infected. However, these methods are nothing more than developments of the leaf disk method (Horsch et al., 1985 (Reference (17))) and not treatments based on novel concepts. The degree of effectiveness and universality of the methods have not been clarified, and they are not used as general methods.

DISCLOSURE OF THE INVENTION

Accordingly, an object of the present invention is to provide a method for promoting efficiency of gene introduction into plant cells, by which gene introduction can be attained simply with a higher efficiency than the conventional gene introduction by *Agrobacterium* method, without injuring the tissue.

The present inventors intensively studied to discover that in the gene introduction method using *Agrobacterium*, the gene introduction efficiency may be significantly promoted by centrifuging the plant cells or plant tissue subjected to the gene introduction, thereby completing the present invention.

That is, the present invention provides a method for promoting efficiency of gene introduction into plant cells by a bacterium belonging to genus *Agrobacterium*, comprising centrifuging said plant cells or plant tissue.

By the present invention, a method for promoting efficiency of gene introduction into plant cells, by which gene introduction can be attained simply with a higher efficiency than the conventional gene introduction by *Agrobacterium* method, without injuring the tissue, has been provided. The method of the present invention may be applied to both monocotyledons and dicotyledons.

Figure 1:
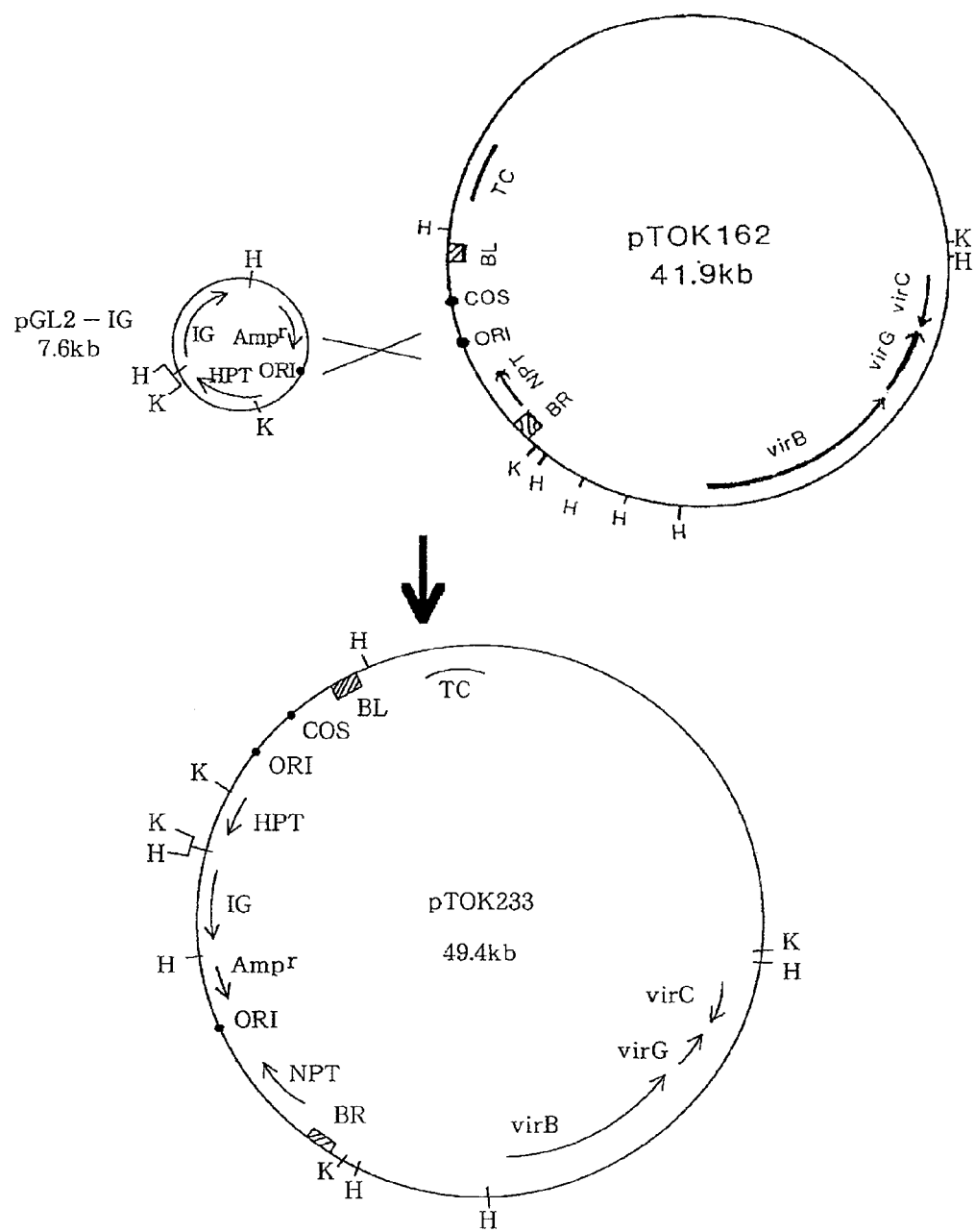
FIG. 1 is a drawing for showing a method for constructing pTOK233 which is an example of super-binary vectors, that may preferably be employed in the present invention.

In the above drawings, the following reference symbols denote the following meanings.

virB: the virB gene in the virulence region of Ti plasmid pTiBo542 contained in *Agrobacterium tumefaciens* A281 virC: the virC gene in the virulence region of Ti plasmid pTiBo542 contained in *Agrobacterium tumefaciens* A281 virG: the virG gene in the virulence region of Ti plasmid pTiBo542 contained in *Agrobacterium tumefaciens* A281

BL: left border sequence of T-DNA of bacteria belonging to genus *Agrobacterium*

BR: right border sequence of T-DNA of bacteria belonging to genus *Agrobacterium*

TC: tetracycline resistant gene

SP: spectinomycin resistant gene

IG: intron GUS gene

HPT: hygromycin resistant gene

K: restriction enzyme KpnI site

H: restriction enzyme HindIII site

Ampr: ampicillin resistant gene

BAR: bar gene

Pnos: promoter of nopaline synthetase gene

Tnos: terminator of nopaline synthetase gene

P35S: CaMV 35S promoter

COS, cos: COS site of λ phage

ORI, ori: replication origin of ColE1

NPT, NPTII kanamycin resistant gene

Vir: entire vir region of Ti plasmid of bacteria belonging to genus *Agrobacterium*

S Vir: entire vir region of Ti plasmid pTiBo542 of super virulent bacteria belonging to genus *Agrobacterium* s vir*: fragment containing a part of vir region of Ti plasmid pTiBo542

BEST MODE FOR CARRYING OUT THE INVENTION

The method of the present invention for promoting efficiency of gene introduction into plant cells by a bacterium belonging to genus *Agrobacterium*, comprises centrifuging the plant cells or plant tissue. The plant cells or plant tissue may be contacted with the bacterium belonging to genus *Agrobacterium* under normal gravity after centrifuging the plant cells or tissue, or the plant cells or tissue may be contacted with the bacterium belonging to genus *Agrobacterium* while centrifuging the plant cells or tissue. Preferably, the plant cells or plant tissue are(is) contacted with the bacterium belonging to genus *Agrobacterium* under normal gravity after centrifuging the plant cells or tissue.

The conditions for centrifugation may appropriately be selected depending on the type of the plant used and the like, and may usually be carried out under a centrifugation acceleration of 100 G to 250,000 G, preferably 500 G to 200,000 G, more preferably 1000 G to 150,000 G. The time for centrifugation may appropriately be selected depending on the centrifugal acceleration, type of the plant used and so on, and is usually and preferably not less than one second. There is no upper limit of the centrifugation time, and about 10 minutes may usually be sufficient for attaining the object of the centrifugation. When the centrifugal acceleration is large, the efficiency of introducing genes may be significantly promoted even if the centrifugation time is very short, for example, 1 second or less. On the other hand, when the centrifugal acceleration is small, the efficiency of introducing genes may be significantly promoted by conducting the centrifugation for a long time. In most cases, especially preferred centrifugation conditions are about 500 G to 200,000 G, especially 1000 G to 150,000 G for about 1 second to 2 hours, and the appropriate centrifugation conditions for the particular plant cells or tissue may be easily selected by a routine experiment.

The method of the present invention is characterized by using the plant cells or plant tissue which were(was) centrifuged, or by contacting the plant cells or plant tissue with a bacterium belonging to the genus *Agrobacterium* while conducting centrifugation, and as the method for gene introduction or transformation per se using the bacterium belonging to the genus *Agrobacterium*, a well-known method may be applied as it is.

The method for gene introduction or transformation per se into plants using a bacterium belonging to the genus *Agrobacterium* is well-known in the art and is widely used.

It is known for a long time that a soil bacterium *Agrobacterium* (*Agrobacterium tumefaciens*) causes crown gall disease in a number of dicotyledons. In 1970s, it was discovered that Ti plasmid concerns the virulence, and that the T-DNA which is a part of Ti plasmid is incorporated into the plant genome. Thereafter, it was proved that the T-DNA contains genes participating in synthesis of hormones (cytokinins and auxins) required for induction of tumor, and that the genes are expressed in plants in spite of the fact that the genes are bacterial genes. A group of genes existing in the virulence region (vir region) in the Ti plasmid is required for the excision of T-DNA and its transfer to plants, and the border sequences existing at the both ends of the T-DNA are necessary for the T-DNA to be excised. *Agrobacterium rhizogenes* which is another bacterium belonging to the genus *Agrobacterium* has a similar system on the Ri plasmid (FIGS. 3 and 4).

Since T-DNA is incorporated into the plant genome by infection of *Agrobacterium*, it was expected that a desired gene may be incorporated into the plant genome by inserting the desired gene in the T-DNA. However, since Ti plasmid is as large as not less than 190 kb, it was difficult to insert a gene into the T-DNA by a standard technique of genetic engineering. Thus, a method for introducing a foreign gene into the T-DNA was developed.

Figure 3:
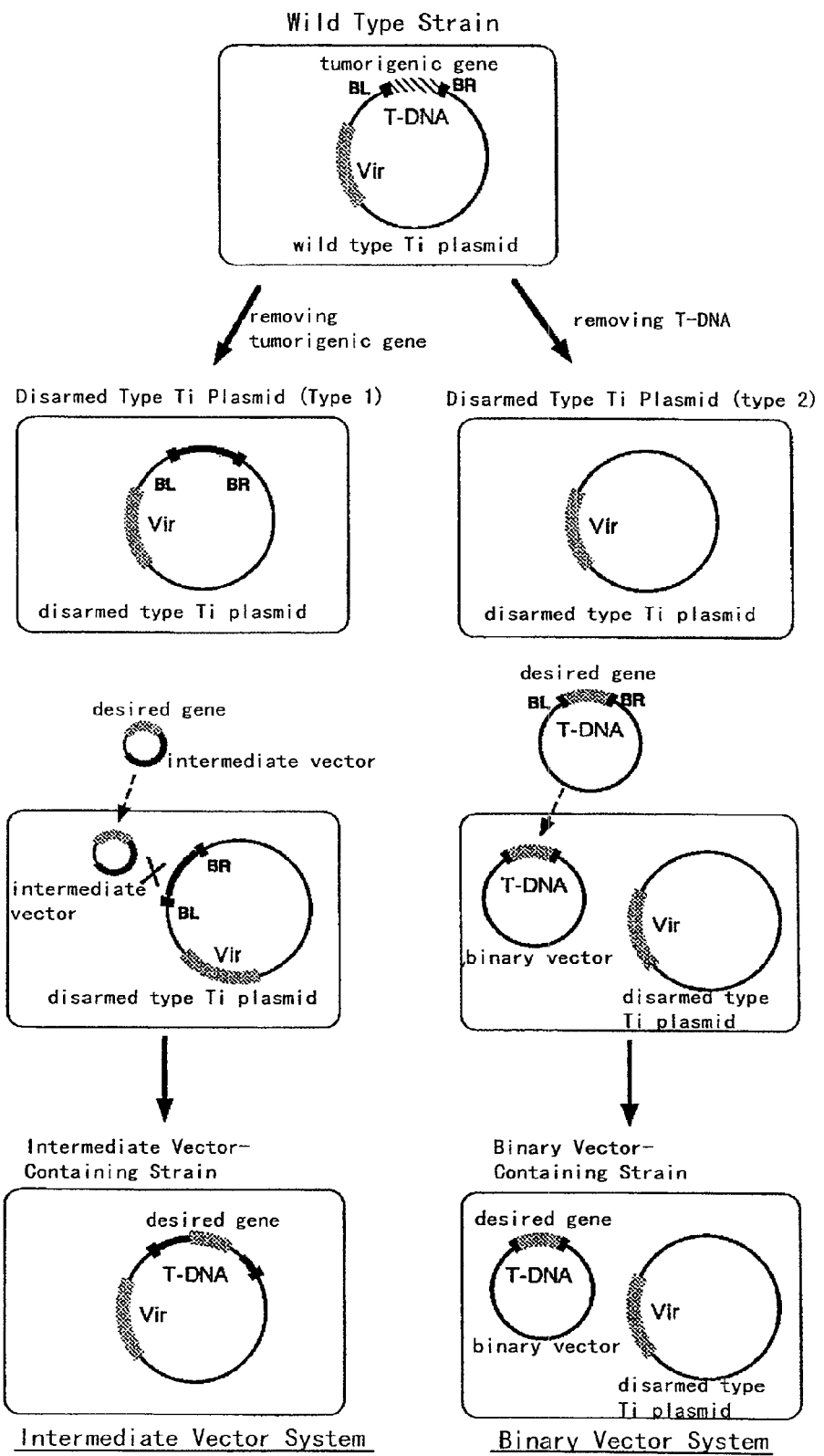
FIG. 3 is a schematic view for showing the intermediate vector system and binary vector system which are major two vector systems of bacteria belonging to genus *Agrobacterium*.
Figure 4:
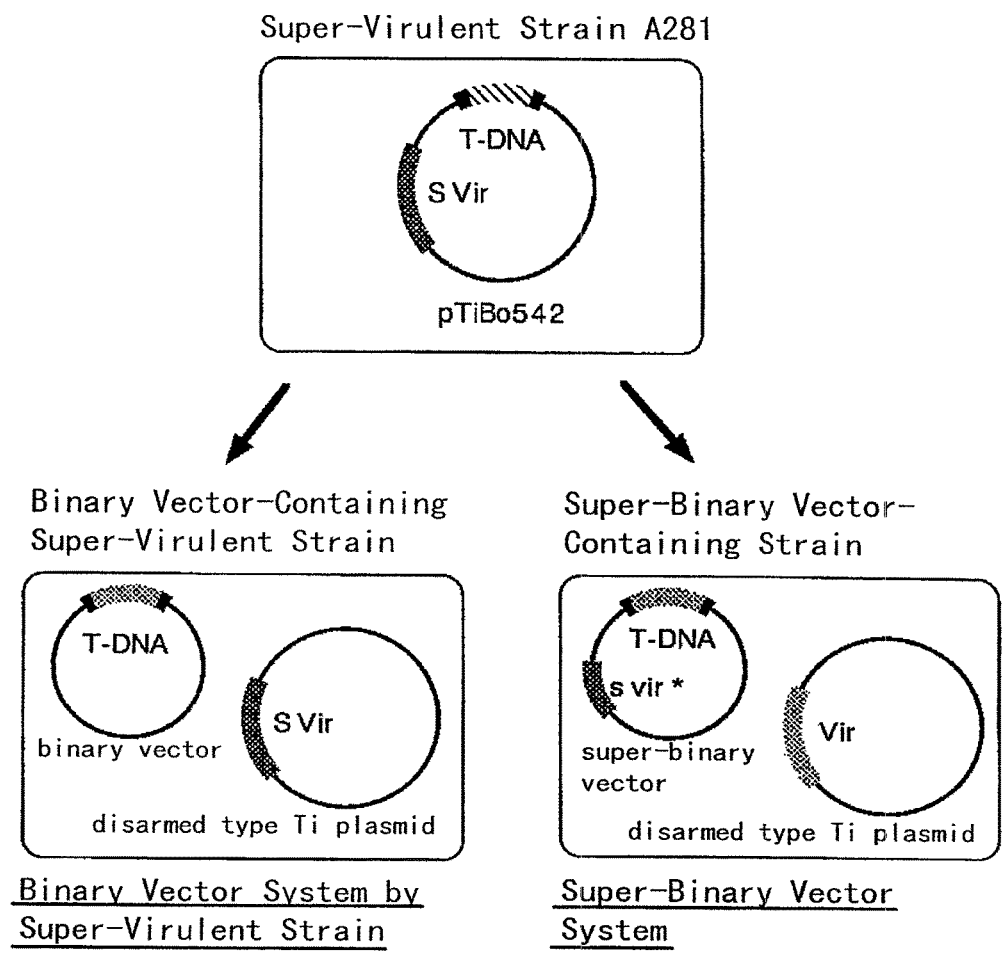
FIG. 4 is a schematic view showing two binary vector systems derived from super virulent strain A281 of *Agrobacterium tumefaciens*.

First, disarmed strains such as LBA4404 (Hoekema et al., 1983 (Reference (12))), C58C1(pGV3850) (Zambryski et al., 1983 (Reference (40))), and GV3Ti11SE (Fraley et al., 1985 (Reference (9))), that have tumorigenic Ti plasmids from which hormone synthetase genes were eliminated, were prepared (FIG. 3). Two methods employing such a strain, that is, a method by which a desired gene is introduced into the Ti plasmid of *Agrobacterium*, and a method by which a T-DNA having a desired gene is introduced into *Agrobacterium*, were developed. One of these methods is the so called intermediate vector method (Fraley et al., 1985 (Reference (9)); Fraley et al., 1983 (Reference (10)); Zambryski et al., 1983 (Reference (40)), Japanese Laid-open Patent Application (Kokai) No. 59-140885 (EP116718)). In this method, an intermediate vector which is easy to handle by genetic manipulation techniques, in which a desired gene may be inserted, and which can be replicated in *E. coli* is introduced into the T-DNA in the disarmed type Ti plasmid of *Agrobacterium* by triparental mating (Ditta et al., 1980 (Reference (8))). Another method is the so called binary vector method (FIG. 3), which is based on the fact that although the vir region is necessary for the T-DNA to be incorporated into plants, it is not necessary that the T-DNA and the vir region exist in the same plasmid ((Hoekema et al., 1983). The vir region contains virA, virB, virC, virD, virE and virG (Plant Biotechnology Encyclopedia (Enterprise Co., Ltd. (1989)), and the vir region is defined as those containing all of virA, virB, virC, virD, virE and virG. Thus, the binary vector is a small plasmid which is replicable in both *Agrobacterium* and *E. coli*, and this plasmid is introduced into *Agrobacterium* having a disarmed type Ti plasmid. The introduction of the binary vector into *Agrobacterium* may be carried out by electroporation method, triparental mating or the like). Binary vector includes pBIN19 (Bevan, 1984 (Reference (4))), pBI121 (Jefferson, 1987 (Reference (19))), pGA482 (An et al., 1988 (Reference (2)), Japanese Laid-open Patent Application (Kokai) No. 60-70080 (EP120516)), and a number of new binary vectors have been constructed based on these vectors. In the system of Ri plasmid, similar vectors have been constructed and are used for transformation.

Agrobacterium A281 (Watson et al., 1975 (Reference (39))) is a super-virulent strain, whose host spectrum is wide and whose efficiency of transformation is higher than other strains (Hood et al., 1987 (Reference (13)); Komari, 1989 (Reference (21))). This feature is brought about by a Ti plasmid pTiBo542 contained in A281 (Hood et al., 1984 (Reference (16)); Jin et al., 1987 (Reference (20)); Komari et al., 1986 (Reference (24))).

Two new systems using pTiBo542 has been developed. One system utilizes strains EHA101 (Hood et al., 1986) and EHA105 (Hood et al., 1993) containing a Ti plasmid which is a disarmed type of pTiBo542. By applying these strains to the above-mentioned binary vector system, a system having a high efficiency of transformation was achieved, which is widely used for transformation of various plants. Another system is "super-binary" vector system (Hiei et al., 1994 (Reference (11)); Ishida et al., 1996 (Reference (18)); Komari et al., 1999 (Reference (26)), WO94/00977, WO95/06722) (FIG. 4). Since this system comprises a disarmed type Ti plasmid having the vir region (virA, virB, virC, virD, virE and virG) (each of these may also be hereinafter referred to as "vir fragment region") and a plasmid having T-DNA, this is a kind of the binary vector system. However, it is different from the binary vector in that a super-binary vector (Komari, 1990a (Reference (22))) in which a vir region fragment (preferably a fragment containing at least virB or virG, more preferably a fragment at least containing virB and virG) substantially lacking at least one of the fragments of vir region is incorporated into the plasmid having the T-DNA, i.e., the binary vector. To introduce a T-DNA region into which a desired gene has been inserted into an Agrobacterium having the super-binary vector, homologous recombination via the triparental mating method may be employed as an easy method (Komari et al., 1996 (Reference (25))). It has been proved that the super-binary vector gives much higher transformation efficiency than the above-described various vector systems for a number of plant species (Hiei et al., 1994 (Reference (11)); Ishida et al., 1996 (Reference (18)); Komari, 1990b (Reference (23)); Li et al., 1996 (Reference (27)); Saito et al., 1992 (Reference (35))).

In the method of the present invention, the host bacterium belonging to the genus Agrobacterium is not restricted, and Agrobacterium tumefaciens (e.g., the above-described Agrobacterium tumefaciens LBA4404 (Hoekema et al., 1983 (Reference (12))) and EHA101 (Hood et al., 1986 (Reference (15))) may preferably be employed.

The method of the present invention may be applied to any of the gene introduction systems as long as it is based on the expression of the group of genes in the vir region in the bacterium belonging to the genus Agrobacterium so as to obtain significant effect. Thus, the method of the present invention may be applied to any of the vector systems such as the above-described intermediate vectors, binary vectors, super-virulent binary vectors and super-binary vectors so as to obtain the advantageous effect of the present invention. The method of the present invention may also be applied to the vector systems obtained by modification of these vectors (e.g., those wherein the entire or a part of the vir region of a bacterium belonging to the genus Agrobacterium is excised and additionally incorporated into the plasmid, or the entire or a part of the vir region of a bacterium belonging to the genus Agrobacterium is excised and is introduced into Agrobacterium as a part of a new plasmid). Further, needless to say, by the method of the present invention, the efficiency of introduction of the T-DNA region of wild type Agrobacterium is promoted so as to promote the infection efficiency.

The desired gene to be introduced into the plant may be inserted into a restriction site in the T-DNA region of the above-described plasmid by a conventional method, and the Agrobacterium into which the desired gene was incorporated may be selected based on an appropriate selection marker such as a drug resistant gene against a drug such as kanamycin or paromomycin. In cases where the plasmid is large and has a number of restriction sites, it is not always easy to insert the desired DNA into the T-DNA region by an ordinary subcloning method. In such a case, the desired DNA may be inserted by the triparental mating method utilizing the homologous recombination in the cell of the bacterium belonging to the genus Agrobacterium.

Introduction of the plasmid into a bacterium belonging to the genus Agrobacterium such as Agrobacterium tumefaciens may be carried out by a known method including the above-mentioned triparental mating method, electroporation method, electroinjection method and chemical treatments with PEG or the like.

The gene which is to be introduced into the plant is, in principle, arranged between the left and right border sequences of the T-DNA as in the conventional method. However, since the plasmid is annular, the plasmid may contain only one border sequence. Alternatively, in cases where a plurality of genes are to be arranged at different sites, the plasmid may contain three or more border sequences. Alternatively, arrangement of the desired plasmid in the Ti or Ri plasmid may be performed in the cell of the bacterium belonging to the genus Agrobacterium, or the desired gene may be arranged in another plasmid. Further, the desired gene may be arranged in a plurality of types of plasmids.

Introduction of a gene into the plant cells via a bacterium belonging to the genus Agrobacterium may be attained by simply making the plant cells or plant tissue contact the bacterium belonging to the genus Agrobacterium. For example, a cell suspension of the bacterium belonging to the genus Agrobacterium having a population density of about $10^6$ to $10^{11}$ cells/ml is prepared, and the plant cells or the plant tissue are(is) immersed in the suspension for about 3 to 10 minutes, followed by co-culturing the resultant on a solid medium for several days, thereby attaining the introduction of the gene.

The cells or the tissue to be subjected to the gene introduction are(is) not restricted at all and may be a leaf, root, stem, fruit or any other portion of the plant. Further, dedifferentiated tissue such as a callus or a non-dedifferentiated tissue such as an embryo may be employed. The type of the plant is not restricted at all, and angiosperms are preferred. As long as the plant is an angiosperm, either dicotyledon or monocotyledon is preferred.

As will be concretely shown in the following Examples, by the method of the present invention, the efficiency of gene introduction is significantly promoted when compared with the conventional Agrobacterium method.

EXAMPLES

The present invention will now be described by way of examples thereof. It should be noted that the present invention is not restricted to the following Examples.

Example 1

(1) *Agrobacterium* Strains and Plasmids

As the *Agrobacterium* and its vectors, LBA4404(pBI121) (pBI121 is commercially available from CLONETECH, U.S., (Jefferson R A 1987 (Reference (19))), LBA4404 (pIG121Hm) (Hiei, Y. et al., 1994 (Reference (11)), LBA4404 (pTOK233) (Hiei et al., 1994 (Reference (11))) and LBA4404 (pSB133) (FIG. 2) were used.

Figure 2:
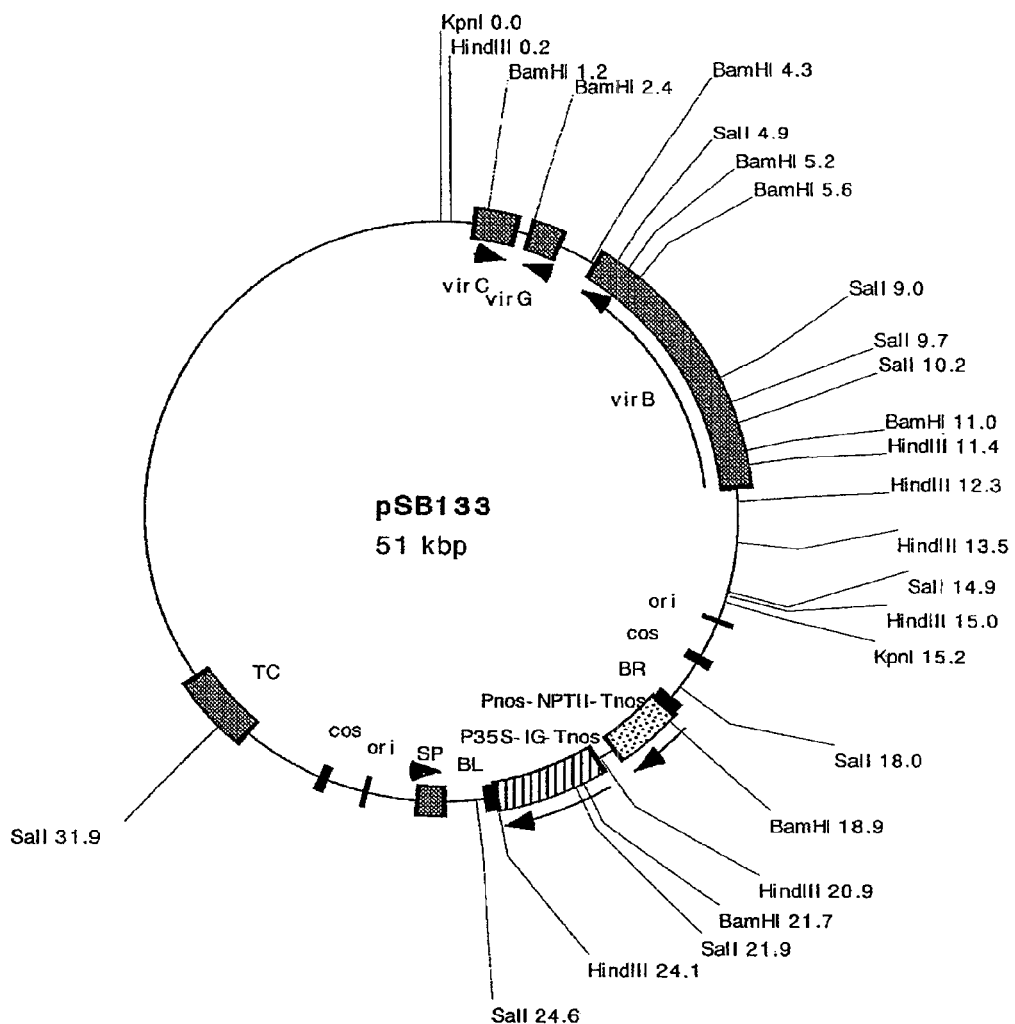
FIG. 2 is a gene map of pSB133 which is an example of super-binary vectors, that may preferably be employed in the present invention.

Construction of pSB133 was carried out as follows: A DNA fragment having a size of 6.2 kb obtained by digesting pGA482 (An G et al., 1985 (Reference (3))) with a restriction enzyme SalI was ligated to a DNA fragment with a size of 5.1 kbp obtained by digesting pSB11 (Komari et al., 1996 (Reference (25)) with Sal I to prepare a plasmid. This plasmid was then digested with restriction enzymes Eco RI and BglII to obtain a DNA fragment with a size of 8.6 kb. This DNA fragment was blunted and a BglII linker (commercially available from TaKaRa) was inserted therein to obtain a plasmid pSB27. The pSB27 was digested with a restriction enzyme HindIII, and a DNA fragment with a size of 3.1 kb containing 35S promoter and an intron-GUS gene, which fragment was obtained by digesting pIG221 (Ohta S et al., 1990 (Reference (32)), was inserted therein to obtain pSB33. The pSB33 was introduced into *E. coli* LE392, and then introduced into *Agrobacterium* LBA4404 containing pSB1 (Komari et al., 1996 (Reference (25))) by triparental mating method (Ditta G et al., 1980 (Reference (8))). The pSB133 was obtained by homologous recombination between pSB1 and pSB33 in the cell of *Agrobacterium*. The T-DNA region of pBI121 contains a kanamycin-resistant gene (nptII) controlled by the promoter of nopaline synthetase gene (nos) and a GUS gene controlled by 35S promoter of cauliflower mosaic virus (CaMV). Each of the T-DNA regions of pIG121Hm and pTOK233 contains an nptII gene controlled by nos promoter, an hpt gene controlled by 35S promoter, and a GUS gene controlled by the 35S promoter, which GUS gene contains introns of the catalase gene of castor bean. The T-DNA region of pSB133 contains an nptII gene controlled by nos promoter and a GUS gene controlled by 35S promoter of CaMV, which GUS gene contains introns of the catalase gene of castor bean (FIG. 2). The plasmids pSB133 and pTOK233 are super-binary vectors having high abilities of transformation (Komari, T. et al., 1999 (Reference (26))).

(2) Sample Varieties and Tissues

As the sample varieties, Koshihikari and Tsukinohikari, which are Japonica rice varieties, were used. Glumes of immature seeds at 8 to 14 days after flowering were removed and the seeds were sterilized with 70% ethanol for several seconds and with 1% aqueous sodium hypochlorite solution containing Tween 20 for 15 minutes. After washing the seeds several times with sterilized water, immature embryos with lengths of 1.5 to 2 mm were excised and used as the sample tissue.

(3) Centrifugation Treatment

The immature embryos of rice were placed in tubes containing sterilized water and centrifuged under an acceleration of 760 G to 150,000 G using a micro high-speed centrifuge, large high-speed centrifuge or an ultra high-speed centrifuge. After the centrifugation, the immature embryos were infected with *Agrobacterium*.

(4) Infection and Co-Culturing

The method for infection to the immature embryos and the method for co-culturing were in accordance with the methods by Hiei et al. (1994) (Reference (11)). That is, after the centrifugation, the sterilized water in each tube was removed and suspension of *Agrobacterium* was added, followed by stirring the mixture with a vortex mixer for 5 to 30 seconds.

The suspensions of bacteria were prepared by collecting colonies of *Agrobacterium* cultured on AB medium (Chilton, M-D et al., 1974 (Reference (6))) with a platinum loop and suspending the collected bacteria in modified AA medium (AA major inorganic salts, AA amino acids and AA vitamins (Toriyama K. et al., 1985 (Reference (36)), MS minor salts (Murashige, T et al., 1962 (Reference (30)), 1.0 g/l casamino acid, 100 µM acetosyringone, 0.2 M sucrose, 0.2 M glucose). After leaving the mixture of immature embryos and the suspension of *Agrobacterium* to stand at room temperature for about 5 minutes, the immature embryos were plated on a medium for co-culturing. As the medium for co-culturing, 2N6-AS medium (Hiei et al. 1994 (Reference (11))) was used except that the inorganic salts thereof were changed to the composition of R2 medium (Ohira et al. 1973 (Reference (31))). It should be noted, however, that the major inorganic salts ($KNO_3$, $KH_2PO_4$, $CaCl_2 2H_2O$, $MgSO_4 7H_2O$) were added to the medium to half concentrations. The density of the bacterial cells to be infected was adjusted to $1 \times 10^8$ to $1 \times 10^9$ cfu/ml. The co-culturing was carried out for 3 to 13 days, and a portion of the immature embryo was treated with X-Gluc to check the expression of the GUS gene (Hiei et al. 1994) (Reference (11)). That is, immediately after the co-culturing, the tissue was immersed in 0.1M phosphate buffer (pH 6.8) containing 0.1% Triton X-100, and was left to stand at 37° C. for 1 hour. After removing *Agrobacterium* with phosphate buffer, phosphate buffer containing 1.0 mM 5-bromo-4-chloro-3-indolyl-β-D-glucuronic acid (X-gluc) and 20% methanol was added. After incubating the resultant at 37° C. for 24 hours, tissueds colored in blue were observed under microscope.

(5) Selection of Transformed Cells

After the co-culturing, the immature embryos and calli were transferred to a primary selection medium containing 250 mg/l carbenicillin and 250 mg/l cefotaxime, and further containing 200 mg/l paromomycin or 10 to 30 mg/l hygromycin, and cultured at 30° C. under luminous condition for 1 to 2 weeks. As the primary selection medium, 2N6K medium described in Hiei et al. (1994) (Reference (11)) supplemented with D-sorbitol to 30 g/l was used (K medium). Further, a medium (N medium) which was the same as the 2N6 medium (inorganic salts and vitamins of N6 (Chu C. C. 1978 (Reference (7))), 1 g/l casamino acid, 2 mg/l 2,4-D) except that the concentration of $(NH_4)_2SO_4$ was changed to 232 mg/l and that the amino acids of AA medium (Toriyama et al., 1985 (Reference (36)) were supplemented was also used in the test.

The calli formed on the primary selection medium were transferred to a secondary selection medium containing 250 mg/l cefotaxime and 250 mg/l carbenicillin, and further containing 200 mg/l paromomycin or 80 mg/l hygromycin, and cultured at 30° C. under luminous condition for 1 to 2 weeks. As the secondary selection medium, a medium which was the same as N6-7 medium described in Hiei et al. (1994) (Reference (11)) except that the concentration of $(NH_4)_2SO_4$ was changed to 232 mg/l and that the amino acids of AA medium (Toriyama et al., 1985 (Reference (36)) were supplemented was used. To the primary and secondary selection media containing paromomycin, agarose was added to 8 g/l as a solidifier. The rate of emerged resistant calli was investigated after the secondary selection.

(6) Regeneration of Transformants

The calli resistant to the selection drugs, obtained from the scutella of immature embryos were plated on N6S3 medium (Hiei et al. 1994 (Reference (11))) for regeneration containing 250 mg/l carbenicillin and 250 mg/l cefotaxime, and further containing 100 mg/l paromomycin or 50 mg/l hygromycin.

(7) Checking GUS Expression in Regenerated Plants

Leaves of the regenerated plants resistant to the drugs, obtained by culturing for regeneration at 25° C. under luminous condition for 4 to 5 weeks were checked for the expression of GUS gene by treating them with X-Gluc in the same manner as mentioned above (Hiei et al. 1994 (Reference (11)). The regenerated plants were transplanted to 500-fold diluted aqueous Hyponex solution and cultivated at 25° C. under luminous condition for about 2 weeks, followed by transplantation to pots in a green house.

(8) Results (i) Discussion about Effects by Centrifugation Treatment

Using a micro high-speed centrifuge, large high-speed centrifuge and an ultra high-speed centrifuge, the effect by the centrifugation treatment to the rice immature embryos was tested. As a result, the efficiency of gene introduction was promoted when the acceleration was within the range of 10 KG to 100 KG (Tables 1, 2, 3 and 6). As for the treatment time, advantageous effect was clearly observed with the treatment for 10 minutes (Tables 4 and 5). The frequency of the transient expression of GUS was not different between the varieties, that is, between Koshihikari and Tsukinohikari. Since not only the effect for promoting the efficiency of gene introduction, but also the effect for inducing formation of callus was observed, it was suggested that centrifugation treatment is effective for induction and growth of calli and in the culturing of plants including other species.

As shown in Table 6, induction of calli from the immature embryos of Tsukinohikari was not at all observed when the centrifugation was carried out at 250 KG for 60 minutes using the ultra high-speed centrifuge. However, induction of calli was observed when the centrifugation was carried out at 110 KG for 60 minutes, and expression of GUS was also observed at high rate. Similarly, as for Koshihikari, induction of calli from the immature embryos of Tsukinohikari was not at all observed when the centrifugation was carried out at 250 KG for 60 minutes using the ultra high-speed centrifuge. From these results, the advantageous effect by centrifugation for rice immature embryo is thought to be obtained at an acceleration between 5 KG to 200 KG. Thus, in view of the simplicity of the treatment, when a micro high-speed centrifuge or a large high-speed centrifuge is used, the treatment at 20 KG or 40 KG is thought to be appropriate. Further, as shown in Tables 9, 10 and 11, it was proved that by the centrifugation treatment at 20 KG for 60 minutes, transformation using immature embryo may be attained not only for LBA4404 (pSB133) having a super-binary vector known to have a high transformation ability, but also for LBA4404 (pIG121Hm) containing an ordinary binary vector.

(ii) Discussion about Centrifugation Treatment and Duration of Co-Culturing

As shown in Tables 7 and 8, the efficiency of GUS expression observed in the transient assay was higher when the duration of co-culturing was 6 or 13 days than when the duration of co-culturing was 3 days. In another experiment, a high GUS expression was observed when the duration of co-culturing was 9 days. Various immature embryos which underwent different durations of co-culturing are now cultured on a primary selection medium (10 ppm hygromycin, 200 ppm paromomycin), and there is a tendency that the rate of emerging of drug resistant calli is smaller in the group co-cultured for 9 or 13 days than in the group co-cultured for 3 or 6 days.

(iii) Examination of Efficiency of Transformation by Centrifugation Treatment

At present, the GUS-positive transformants (Tables 4 and 5) prepared as described above are acclimatized, and culturing is continued. For some lines, seeds were collected and fertility was checked. As a result, no differences in morphology and fertility between the centrifuged transformants and the non-treated transformants (Koshihikari and Tsukinohikari) were observed.

Hiei et al. (1994 (Reference (11))) reported that transformation may be attained with a relatively high efficiency using calli of rice. Aldemita R R et al. 1996 (Reference (1))) reported a case of transformation using rice immature embryo. To more effectively and more stably carry out these transformation methods, the above-described centrifugation treatment method is very effective. Especially, although the quality of immature embryo is likely varied depending on the environment of culturing so that it is not easy to always obtain immature embryo suited for transformation, it may be possible to keep high efficiency of transformation by subjecting the immature embryo to the centrifugation treatment. Hiei et al. (1994) (Reference (11)) showed that a super-binary vector having a high transformation ability promotes the efficiency of transformation of rice. According to Aldemita R R et al. 1996 (Reference (1))), transformants were obtained only in the test using LBA4404 (pTOK233) containing a super-binary vector. By the centrifugation treatment method according to the present invention, even when an ordinary binary vector is used, a high efficiency of transformation is attained, which is comparable to or even higher than that attained in the transformation using a super-binary vector. Further, by employing both the super-binary vector and the centrifugation treatment method, the efficiency may be even more promoted. Still further, it is expected that transformants may be obtained by employing the centrifugation treatment method for the varieties with which a transformant has not hitherto been obtained.

TABLE 1

Various Centrifugation Treatments and Results of GUS Expression after Co-culturing (Sample Strain: LBA4404/pSB133)

| Variety | Population Density of Infected Bacterium (cfu/ml) | Not Treated | Centrifugal Acceleration | | |
|---|---|---|---|---|---|
| | | | 760 G | 8,500 G | 19,100 G |
| Koshihikari | $1 \times 10^8$ | 3/10(+) | 6/10(+) | 7/10(++) | 7/10(+++) |
| | $1 \times 10^9$ | 2/10(+) | 0/10(—) | 4/10(++) | 7/10(+++) |
| Tsukino-hikari | $1 \times 10^8$ | 4/10(+) | 3/10(+) | 9/10(+++) | 7/10(+++) |
| | $1 \times 10^9$ | 1/10(+) | 6/10(++) | 2/10(+) | 7/10(+++) |

Time of Centrifugation Treatment: 10 minutes; Duration of Co-culturing: 3 to 5 days;
Number of GUS-positive immature embryos/Number of sample immature embryos
The symbols in parentheses indicate the area of the region in scutella in which GUS was expressed. —: none; +: small; ++: medium; +++: large

TABLE 2

Rate of Emerging of Paromomycin-resistant Calli from Koshihikari Immature Embryos (Sample Strain: LBA4404/pSB133)

| Selection Medium | Population Density of Infected Bacterium (cfu/ml) | Not Treated | Centrifugal Acceleration | | |
|---|---|---|---|---|---|
| | | | 760 G | 8,500 G | 19,100 G |
| N medium | $1 \times 10^8$ | 4.8%(1/21) | 0.0%(0/22) | 15.0%(3/20) | 31.8%(7/22) |
| | $1 \times 10^9$ | 4.3%(1/23) | 4.5%(1/22) | 16.7%(3/18) | 13.3%(2/15) |
| K medium | $1 \times 10^8$ | 0.0%(0/21) | 0.0%(0/22) | 14.3%(3/21) | 18.2%(4/22) |
| | $1 \times 10^9$ | 0.0%(0/23) | 0.0%(0/21) | 0.0%(0/19) | 0.0%(0/22) |

Number of immature embryos from which resistant calli were derived/Number of sample immature embryos, checked after completion of the secondary selection
Time of Centrifugation Treatment: 10 minutes; Duration of Co-culturing: 3 to 5 days

TABLE 3

Rate of Emerging of Paromomycin-resistant Calli from Tsukinohikari Immature Embryos (Sample Strain: LBA4404/pSB133)

| Selection Medium | Population Density of Infected Bacterium (cfu/ml) | Not Treated | Centrifugal Acceleration | | |
|---|---|---|---|---|---|
| | | | 760 G | 8,500 G | 19,100 G |
| N medium | $1 \times 10^8$ | 0.0%(0/11) | 0.0%(0/11) | 30.0%(3/10) | 36.4%(4/11) |
| | $1 \times 10^9$ | 0.0%(0/11) | 9.1%(1/11) | 27.3%(3/11) | 54.5%(6/11) |
| K medium | $1 \times 10^8$ | 0.0%(0/10) | 0.0%(0/15) | 9.1%(1/11) | 9.1%(1/11) |
| | $1 \times 10^9$ | 0.0%(0/11) | 0.0%(0/11) | 0.0%(0/11) | 45.5%(5/11) |

Number of immature embryos from which resistant calli were derived/Number of sample immature embryos, checked after completion of the secondary selection
Time of Centrifugation Treatment: 10 minutes; Duration of Co-culturing: 3 to 5 days

TABLE 4

Time of Centrifugation Treatment and Results of GUS Expression after Co-culturing

| Strains and Plasmids | Not Treated | Time of Centrifugation Treatment | | |
|---|---|---|---|---|
| | | 10 minutes | 30 minutes | 60 minutes |
| LBA4404(pSB133) | 9/10(+) | 9/10(++) | 10/10(++) | 10/10(+++) |
| LBA4404(pTOK233) | 9/10(+) | 10/10(++) | 10/10(++) | 10/10(+++) |

Centrifugal acceleration: 20,000 G; Sample Variety: Koshihikari; Number of GUS-positive immature embryos/Number of sample immature embryos area of the region in scutella in which GUS was expressed. +: small; ++: medium; +++: large

TABLE 5

Time of Centrifugation Treatment and Rate of Emerging of Paromomycin-resistant Calli (Variety: Koshihikari)

| Selection Medium | Culturing Condition | Not Treated | Time of Centrifugation Treatment | | |
|---|---|---|---|---|---|
| | | | 10 minutes | 30 minutes | 60 minutes |
| N medium | Luminous (30° C.) | 0.0%(0/31) | 34.3%(12/35) | 35.0%(14/40) | 53.3%(16/30) |
| | Dark (30° C.) | 0.0%(0/32) | 54.1%(20/37) | 34.2%(13/38) | 58.6%(17/29) |

TABLE 5-continued

Time of Centrifugation Treatment and Rate of Emerging of Paromomycin-resistant Calli (Variety: Koshihikari)

| Selection Medium | Culturing Condition | Not Treated | 10 minutes | 30 minutes | 60 minutes |
|---|---|---|---|---|---|
| K medium | Luminous (30° C.) | 0.0%(0/31) | 20.0%(7/35) | 38.5%(15/39) | 40.0%(12/30) |
|  | Dark (30° C.) | 0.0%(0/32) | 48.6%(17/35) | 41.0%(16/39) | 33.3%(10/30) |

Centrifugal acceleration: 20,000 G; Duration of Co-culturing: 3 to 5 days, checked after completion of the secondary selection
Number of immature embryos from which resistant calli were derived/Number of sample immature embryos

TABLE 6

Intensity of Centrifugation Treatment and GUS Expression after Co-culturing (variety: Tsukinohikari)

| Centrifugation Treatments | Duration of Co-culturing | — | ± | + | ++ |
|---|---|---|---|---|---|
| Not Treated | 3 days | 6 | 4 | 0 | 0 |
|  | 6 days | 0 | 2 | 6 | 2 |
| 20 KG [1] | 3 days | 0 | 0 | 2 | 8 |
|  | 6 days | 0 | 0 | 2 | 8 |
| 40 KG [2] | 3 days | 1 | 0 | 1 | 8 |
|  | 6 days | 0 | 0 | 0 | 10 |
| 110 KG [3] | 3 days | 1 | 0 | 5 | 4 |
|  | 6 days | 0 | 0 | 2 | 8 |
| 250 KG [3] | 3 days | 10 | 0 | 0 | 0 |
|  | 6 days | 10 | 0 | 0 | 0 |

Sample Strain: LBA4404/pIG121Hm; Time of Centrifugation Treatment: 60 minutes
[1] micro high-speed centrifuge;
[2] large high-speed centrifuge;
[3] ultra high-speed centrifuge
Rate of GUS-expressed area in scutella: —: none; ±: <1/8; +: 1/8-1/4; ++: >1/4

TABLE 7

Centrifugation Treatment, Duration of Co-culturing and GUS Expression after Co-culturing (Variety: Tsukinohikari)

| Centrifugation Treatments | Duration of Co-culturing | — | ± | + | ++ |
|---|---|---|---|---|---|
| Not Treated | 3 days | 5 | 4 | 1 | 0 |
|  | 6 days | 0 | 6 | 2 | 2 |
|  | 13 days | 0 | 5 | 2 | 3 |
| 20 KG [1] | 3 days | 0 | 2 | 5 | 3 |
|  | 6 days | 0 | 1 | 3 | 6 |
|  | 13 days | 0 | 1 | 3 | 6 |
| 40 KG [2] | 3 days | 0 | 1 | 7 | 2 |
|  | 6 days | 0 | 0 | 8 | 2 |
|  | 13 days | 0 | 1 | 5 | 4 |

Sample Strain: LBA4404/pIG121Hm;
[1] micro high-speed centrifuge;
[2] large high-speed centrifuge; Centrifugation was carried out for 60 minutes at the indicated revolution.
Rate of GUS-expressed area in scutella: —: none; ±: <1/8; +: 1/8-1/4; ++: >1/4

TABLE 8

Centrifugation Treatment, Duration of Co-culturing and GUS Expression after Co-culturing (Variety: Koshihikari)

| Centrifugation Treatments | Duration of Co-culturing | — | ± | + | ++ |
|---|---|---|---|---|---|
| Not Treated | 3 days | 7 | 3 | 0 | 0 |
|  | 6 days | 3 | 1 | 0 | 0 |
|  | 13 days | 1 | 6 | 2 | 1 |
| 20 KG [1] | 3 days | 0 | 0 | 1 | 9 |
|  | 6 days | 0 | 0 | 2 | 8 |
|  | 13 days | 0 | 0 | 1 | 9 |
| 40 KG [2] | 3 days | 1 | 0 | 4 | 5 |
|  | 6 days | 0 | 0 | 0 | 10 |
|  | 13 days | 0 | 0 | 1 | 9 |

Sample Strain: LBA4404/pIG121Hm;
[1] micro high-speed centrifuge;
[2] large high-speed centrifuge; Centrifugation was carried out for 60 minutes at the indicated revolution.
Rate of GUS-expressed area in scutella: —: none; ±: <1/8; +: 1/8-1/4; ++: >1/4

TABLE 9

Results of Transformation by LBA4404(pBI121) (Variety: Tsukinohikari)

| Treatments | Number of Immature Embryos | Number of Acclimatized Plants | Number of GUS-positive Plants | Transformation Efficiency |
|---|---|---|---|---|
| Not Treated | 50 | 17 | 12 | 24.0(%) |
| Centrifugation Treatment | 150 | 60 | 54 | 36.0(%) |

Centrifugation Treatment: 20 KG-60 minutes; Duration of Co-culturing: 5 days

TABLE 10

Results of Transformation by LBA4404(pIG121Hm) (Variety: Tsukinohikari)

| Treatments | Number of Immature Embryos | Number of Acclimatized Plants | Number of GUS-positive Plants | Transformation Efficiency |
|---|---|---|---|---|
| Not Treated | 40 | 9 | 3 | 7.5(%) |
| Centrifugation Treatment | 47 | 10 | 5 | 10.6(%) |

Centrifugation Treatment: 20 KG-60 minutes; Duration of Co-culturing: 5 days

TABLE 11

Results of Transformation by LBA4404(pBI121)
(Variety: Koshihikari)

| Treatments | Number of Immature Embryos | Number of Acclimatized Plants | Number of GUS-positive Plants | Transformation Efficiency |
|---|---|---|---|---|
| Not Treated | 49 | 4 | 2 | 4.1(%) |
| Centrifugation Treatment | 274 | 35 | 27 | 9.9(%) |

Centrifugation Treatment: 20 KG-60 minutes; Duration of Co-culturing: 5 days

TABLE 12

Results of Transformation by LBA4404(pSB133)
(Variety: Koshihikari)

| Treatments | Number of Immature Embryos | Number of Acclimatized Plants | Number of GUS-positive Plants | Transformation Efficiency |
|---|---|---|---|---|
| Not Treated | 63 | 0 | — | 0.0(%) |
| Centrifugation Treatment | 281 | 30 | 23 | 8.2(%) |

Centrifugation Treatment: 20 KG-60 minutes; Duration of Co-culturing: 3 days

Example 2

Immature embryos of maize with a size of about 1.2 mm (variety: A188, obtained from National Institute of Agrobiological Resources, The Ministry of Agriculture, Forestry and Fisheries) were aseptically collected and washed once with LS-inf liquid medium. To a centrifugal tube containing the immature embryo and 2.0 ml of LS-inf medium containing 100 µM acetosyringone, a suspension of *Agrobacterium tumefaciens* LBA4404(pSB131) (Ishida et al. 1996 (Reference (18))) was added to a population density of about $1 \times 10^9$ cfu/ml, and the resulting mixture was centrifuged at 40,000 G, at 4° C. for 30 minutes. The control embryo was left to stand in the same cell suspension at room temperature for 30 minutes. After the treatment, the mixture was gently stirred and plated on LS-AS medium such that the surface of hypocotyl contacts the medium. On the other hand, infection to immature embryos after centrifugation treatment was carried out as follows: Embryos aseptically collected were washed once with LS-inf liquid medium and transferred to centrifugation tubes containing the same medium, followed by centrifugation treatment at 20 KG or 40 KG at 4° C. for 1 hour. The control sample was left to stand in the liquid medium at room temperature for 1 hour. After the treatment, the liquid medium was removed, and a suspension of LBA4404 (pSB131) with a population density of about $1 \times 10^9$ cfu/ml was added, followed by gently stirring of the mixture. After leaving the mixture to stand at room temperature for 5 minutes, the embryos were plated on LS-AS medium containing 10 µM $AgNO_3$ such that the surface of each hypocotyl contacts the medium. After co-culturing in the dark at 25° C. for 3 days, an aliquot of the immature embryos was sampled and the transient expression of the GUS gene was checked by the treatment with X-gluc as in Example 1. The above-described medium and method for culturing were in accordance with Ishida, Y. et al. 1996 (Reference (18)).

The transient expression of the GUS gene in the A188 immature embryos infected with LBA4404 (pSB131) is shown in Table 13. Although any embryo showed expression of the GUS gene, a number of the immature embryos subjected to the centrifugation treatment showed expression in larger area than the control immature embryos. The increase in the gene-introduced sites by the centrifugation treatment was observed in both cases wherein the centrifugation treatment was performed together with the *Agrobacterium* and wherein the *Agrobacterium* was infected after the centrifugation treatment. Further, expression of the GUS gene was observed in larger area than in the control even if the intensity of centrifugation and the time of treatment were changed.

By these results, the possibility that by culturing the immature embryos after centrifugation treatment on a selection medium, transformed plants are obtained at higher efficiency than the control was suggested. Further, the possibility that the maize varieties (Ishida et al. 1996 (Reference (18))) other than A188, which could not be hitherto transformed by the conventional *Agrobacterium* method, may be transformed by the centrifugation treatment, was suggested.

TABLE 13

Transient Expression of GUS Gene in A188 Immature Embryos

| Test | Treatment KG | min | Number of Sample Immature Embryos | Expression of GUS Gene +++ | ++ | + | − |
|---|---|---|---|---|---|---|---|
| 1 | 40 | 30 | 27 | 7 | 10 | 10 | 0 |
|  | Control | 30 | 30 | 1 | 17 | 12 | 0 |
| 2 | 40 | 60 | 20 | 0 | 3 | 17 | 0 |
|  | 20 | 60 | 20 | 0 | 10 | 10 | 0 |
|  | Control | 60 | 20 | 0 | 1 | 19 | 0 |

Control was treated under 1G
In Test 1, centrifugation treatment was performed in the presence of *Agrobacterium*.
In Test 2, *Agrobacterium* was infected after the centrifugation treatment.

REFERENCES (1) Aldemita R R, Hodges T K (1996) *Agrobacterium tumefaciens*-mediated transformation of japonica and indica rice varieties. Planta 199: 612-617
(2) An, G., Evert, P. R., Mitra, A. and Ha, S. B. (1988) Binary vectors. In Gelvin, S. B. and Schilperoort, R. A. (eds.), Plant Molecular Biology Manual A3. Kluwer Academic Press, Dordrecht, pp. 1-19.
(3) An, G., Watson, B D., Stachel, S., Gordon, M P. & Nester, E W., (1985) New cloning vehicles for transformation of higher plants. EMBO J., 4:277-288.
(4) Bevan, M. (1984) Binary *Agrobacterium* vectors for plant transformation. Nucleic Acids Res., 12, 8711-8721.
(5) Bidney, D., Scelonge, C., Martich, J., Burrus, M., Sims, L., and Huffmanm G. (1992) Microprojectile bombardment of plant tissues increases transformation frequency by *Agrobacterium tumefaciens*. Plant Mol. Biol., 18, 301-313.
(6) Chilton, M-D., Currier, T C. Farrand, S K. Bendich, A J. Gordon, M P. & Nester E W. (1974) *Agrobacterium tumefaciens* DNA and PS8 bacteriophage DNA not detected in crown gall tumers. Proc. Natl. Acad. Sci. USA, 71:3672-3676
(7) Chu, C. C., (1978) Proc. Symp. Plant Tissue Culture, Science Press Peking, pp.43-50
(8) Ditta, G., Stanfield, S., Corbin, D. and Helinski, D. R. (1980) Broad host range DNA cloning system for Gram-negative bacteria: Construction of gene bank of *Rhizobium meliloti*. Proc. Natl. Acad. Sci. USA, 77, 7347-7351.

(9) Fraley, R. T., Rogers, S. G., Horsch, R. B., Eicholtz, D. A. and Flick, J. S. (1985) The SEV system: a new disarmed Ti plasmid vector for plant transformation. Bio/technology, 3, 629-635.

(10) Fraley, R. T., Rogers, S. G., Horsch, R. B., Sanders, P. R., Flick, J. S., Adams, S. P., Bittner, M. L., Brand, L. A., Fink, C. L., Fry, J. S., Galluppi, G. R., Goldberg, S. B., Hoffmann, N. L. and Woo, S. C. (1983) Expression of bacterial genes in plant cells.

(11) Hiei, Y., Ohta, S., Komari, T. and Kumashiro, T. (1994) Efficient transformation of rice (Oryza sativa L.) mediated by Agrobacterium and sequence analysis of the boundaries of the T-DNA. The Plant Journal, 6, 271-282.

(12) Hoekema, A., Hirsch, P. R., Hooykaas, P. J. J. and Schilperoort, R. A. (1983) A binary plant vector strategy based on separation of vir- and T-region of the Agrobacterium tumefaciens Ti-plasmid. Nature, 303, 179-180.

(13) Hood, E. E., Fraley, R. T. and Chilton, M.-D. (1987) Virulence of Agrobacterium tumefaciens strain A281 on legumes. Plant Physiol, 83, 529-534.

(14) Hood, E. E., Gelvin, S. B., Melchers, L. S. and Hoekema, A. (1993) New Agrobacterium helper plasmids for gene transfer to plants. Transgenic Res., 2, 208-218.

(15) Hood, E. E., Helmer, G. L., Fraley, R. T. and Chilton, M.-D. (1986) The hypervirulence of Agrobacterium tumefaciens A281 is encoded in a region of pTiBo542 outside of T-DNA. J. Bacteriol., 168, 1291-1301.

(16) Hood, E. E., Jen, G., Kayes, L., Kramer, J., Fraley, R. T. and Chilton, M.-D. (1984) Restriction endonuclease map of pTiBo542, a potential Ti-plasmid vector for genetic engineering of plants. Bio/technology, 2, 702-709.

(17) Horsch, R. B., Fry, J. E., Hoffmann, N. L., Eichholtz, D., Rpgers, S. G. and Fraley, R. T. (1985) A simple and general method for transferring genes into plants. Science 227, 1229-1231.

(18) Ishida, Y., Saito, H., Ohta, S., Hiei, Y., Komari, T. and Kumashiro, T. (1996) High efficiency transformation of maize (Zea mays L.) mediated by Agrobacterium tumefaciens. Nature Biotechnol, 14, 745-750.

(19) Jefferson, R. A. (1987) Assaying chimeric genes in plants: the GUS gene fusion system. Plant Mol. Biol. Rep., 5, 387-405.

(20) Jin, S., Komari, T., Gordon, M. P. and Nester, E. W. (1987) Genes responsible for the supervirulence phenotype of Agrobacterium tumefaciens A281. J. Bacteriol., 169, 4417-4425.

(21) Komari, T. (1989) Transformation of callus cultures of nine plant species mediated by Agrobacterium. Plant Sci., 60, 223-229.

(22) Komari, T. (1990a) Genetic characterization of double-flowered tobacco plant obtained in a transformation experiment. Theor. Appl. Genet., 80, 167-171.

(23) Komari, T. (1990b) Transformation of cultured cells of Chenopodium quinoa by binary vectors that carry a fragment of DNA from the virulence region of pTiBo542. Plant Cell Reports, 9, 303-306.

(24) Komari, T., Halperin, W. and Nester, E. W. (1986) Physical and functional map of supervirulent Agrobacterium tumefaciens tumor-inducing plasmid pTiBo542. J. Bacteriol., 166, 88-94.

(25) Komari, T., Hiei, Y., Saito, Y., Murai, N. and Kumashiro, T. (1996) Vectors carrying two separate T-DNAs for co-transformation of higher plants mediated by Agrobacterium tumefaciens and segregation of transformants free from selection markers. Plant J, 10, 165-174.

(26) Komari, T. and Kubo, T. (1999) Methods of Genetic Transformation: Agrobacterium tumefaciens. In Vasil, I. K. (ed.) Molecular improvement of cereal crops. Kluwer Academic Publishers, Dordrecht, pp. 43-82.

(27) Li, H.-Q., Sautter, C., Potrykus, I. and Puonti-Kaerlas, J. (1996) Genetic transformation of cassava (Manihot esculenta Crantz). Nature Biotechnol., 14, 736-740.

(28) Lindsey, K., Gallois, P. and Eady, C. (1991) Regeneration and transformation of sugarbeet by Agrobacterium tumefaciens. Plant Tissue Culture Manual B7:1-13. Kluwer Academic Publishers.

(29) McCormick, S. (1991) Transformation of tomato with Agrobacterium tumefaciens. Plant Tissue Culture Manual B6:1-9, Kluwer Academic Publishers.

(30) Murashige, T. and Skoog, F. (1962) Physiol. Plant 15:473-497.

(31) Ohira, K., Ojima, K., Fujiwara, A. (1973) Studies on the nutrition of rice cell culture I. A simple, defined medium for rapid growth in suspension culture. Plant Cell Physol., 14:1113-1121.

(32) Ohta, S., Mita, S., Hattori, T., Namamura, K. (1990) Construction and expression in tobacco of a β-glucuronidase (GUS) reporter gene containing an intron within the coding sequence. Plant Cell Physiol. 31: 805-813.

(33) Potrykus, I., Bilang, R., Futterer, J., Sautter, C. and Schrott, M. (1998) Agricultural Biotecnology, NY:Mercel Dekker Inc. pp. 119-159.

(34) Rogers, S. G., Horsch, R. B. and Fraley, R. T. (1988) Gene transfer in plants: Production of transformed plants using Ti plasmid vectors. Method for Plant Molecular Biology, CA: Academic Press Inc. pp.423-436.

(35) Saito, Y., Komari, T., Masuta, C., Hayashi, Y., Kumashiro, T. and Takanami, Y. (1992) Cucumber mosaic virus-tolerant transgenic tomato plants expressing a satellite RNA. Theor. Appl. Genet., 83, 679-683.

(36) Toriyama, K. and Hinata, K. (1985) Plant Set. 41:179-183

(37) Trick, H. N. and Finer, J. J. (1997) SAAT: sonication-assisted Agrobacterium-mediated transformation. Transgenic Research 6:329-336.

(38) Visser, R. G. F. (1991) Regeneration and transformation of potato by Agrobacterium tumefaciens. Plant Tissue Culture Manual B5:1-9. Kluwer Academic Publishers.

(39) Watson, B., Currier, T. C., Gordon, M. P., Chilton, M.-D. and Nester, E. W. (1975) Plasmid required for virulence of Agrobacterium tumefaciens. J Bacteriol, 123, 255-264.

(40) Zambryski, P., Joos, H., Genetello, C., Leemans, J., Van Montagu, M. and Schell, J. (1983) Ti plasmid vector for the introduction of DNA into plant cells without alteration of their normal regeneration capacity. EMBO J, 2, 2143-2150.

The invention claimed is:

1. An Agrobacterium-mediated transformation method for transforming a monocotyledonous embryo with a desired gene comprising:
   centrifuging the monocotyledonous embryo under a centrifugal acceleration of 1000 G to 150,000 G; and
   contacting the monocotyledonous embryo with Agrobacterium, wherein said Agrobacterium includes the desired gene, and wherein said centrifugation promotes efficiency of the transformation of the desired gene into said embryo, said contacting step being carried out after or simultaneously to said centrifugation.

2. The method according to claim 1, wherein said monocotyledonous embryo belongs to the family Gramineae.

3. The method according to claim 2, wherein said monocotyledonous embryo is rice or maize.

4. The method according to claim 1, wherein said contacting is carried out after centrifuging said monocotyledonous embryo.

5. The method according to claim 4, wherein said centrifugation is carried out for 1 second to 4 hours.

6. The method according to claim 5, wherein said centrifugation is carried out for 5 minutes to 2 hours.

7. The method according to claim 1, wherein said centrifugation is carried out for 5 minutes to 2 hours and wherein said monocotyledonous embryo is rice or maize.

8. An *Agrobacterium*-mediated transformation method for promoting efficiency of gene introduction into a monocotyledonous embryo with a desired gene comprising:
   centrifuging the monocotyledonous embryo under a centrifugal acceleration of 8,500 G to 110,000 G, wherein said centrifugation is carried out from 5 minutes to 2 hours; and
   contacting the monocotyledonous embryo with *Agrobacterium*, wherein said *Agrobacterium* includes the desired gene, and wherein said centrifugation promotes efficiency of the transformation of the desired gene into said embryo, said contacting step being carried out after or simultaneously to said centrifugation.

9. The method according to claim 1, wherein said monocotyledonous embryo is an immature embryo.

10. The method according to claim 8, wherein said monocotyledonous embryo is an immature embryo.

\* \* \* \* \*